United States Patent [19]

White et al.

[11] 4,110,369
[45] Aug. 29, 1978

[54] PROCESS FOR THE PREPARATION OF UNSATURATED ACIDS FROM UNSATURATED ALDEHYDES

[75] Inventors: James F. White, Akron; Wilfrid G. Shaw, Lyndhurst, both of Ohio

[73] Assignee: The Standard Oil Company, Cleveland, Ohio

[21] Appl. No.: 733,736

[22] Filed: Oct. 19, 1976

[51] Int. Cl.$^2$ ............................................. C07C 51/32
[52] U.S. Cl. ................................. 260/530 N; 252/435; 252/437
[58] Field of Search ................. 260/530 N; 252/435, 252/437

[56] References Cited

U.S. PATENT DOCUMENTS

| 3,939,096 | 2/1976 | Richardson | 260/530 N |
| 3,956,377 | 5/1976 | Dolhyj et al. | 260/530 N |

FOREIGN PATENT DOCUMENTS 2,353,131  4/1975  Fed. Rep. of Germany ...... 260/530 N

*Primary Examiner*—Vivian Garner
*Attorney, Agent, or Firm*—Gwenetta Douglas Hill; Herbert D. Knudsen; Larry W. Evans

[57] ABSTRACT

Coated catalysts having an inert support material with an outer surface and a coating of active catalyst containing molybdenum, phosphorus, arsenic, copper and oxygen have been found to be especially effective catalysts for the production of unsaturated acids from the corresponding unsaturated aldehydes, for example, methacrolein is oxidized to methacrylic acid using these catalysts. The catalysts give a very low exotherm, very high single pass yields of the desired acid and reduce the undesirable byproducts.

13 Claims, No Drawings

PROCESS FOR THE PREPARATION OF UNSATURATED ACIDS FROM UNSATURATED ALDEHYDES

BACKGROUND OF THE INVENTION

Use of a catalyst employing molybdenum, phosphorus, arsenic, copper and ammonium is shown in West German Provisional Pat. No. 2,353,131. Catalysts containing oxides of molybdenum, arsenic, phosphorus and optionally cobalt, aluminum or copper on a support having external macropores are disclosed in U.S. Pat. No. 3,761,516.

Unexpectedly higher yields and selectivities of acrylic acid and methacrylic acid are obtained using the coated catalysts of the invention.

SUMMARY OF THE INVENTION

It has been discovered in the process for the preparation of acrylic acid or methacrylic acid by the oxidation of acrolein or methacrolein in the presence of an active oxide catalyst of the formula $$Mo_{12}P_bAs_cCu_dO_f$$

wherein
 $b$, $c$ and $d$ are numbers from 0.001 to 10;
 $f$ is the number of oxygens required by the valence states of the other elements present,
at an elevated temperature of about 200° to about 500° C., that using a coated catalyst consisting essentially of an inert support material having an outer surface and a continuous coating of said active catalyst on said inert support strongly adhering to the outer surface of said support affords an improved process.

By use of these coated catalysts in the reaction to produce unsaturated acids, a very low exotherm is realized allowing for better control of the reaction. High single pass yields are exhibited and the elimination of undesirable byproducts is obtained.

The central aspect of the present invention is the special coated catalyst employed. The special coated catalyst consists of an inner-support material having an outer surface and a uniform coating of the active catalytic material on this outer surface. These catalysts can be prepared by a number of different methods.

The support material for the catalyst forms the inner core of the catalyst. This is an essentially inert support and may have substantially any particle size although a diameter of at least 20 microns is preferred. Especially preferred in the present invention for use in a commercial reactor are those supports which are spherical and which have a diameter of about 0.2 cm. to about 2 cm.

By the preferred procedure of the invention, the support material employed is at least partially porous. By this is meant the support material must be susceptible to the penetration of liquid. Preferred support materials are capable of absorbing at least about 1% by weight of water based upon the weight of the support. Suitable examples of essentially inert support materials include: Alundum, silica, alumina, alumina-silica, silicon carbide, titania and zirconia. Especially preferred among these supports are Alundum, silica, alumina and alumina-silica.

The catalysts may contain essentially any portions of support and catalytically active material. Preferred catalysts contain about 10 to about 100 percent by weight of catalytically active material based on the weight of the support.

The total coated catalyst of the present invention is conveniently prepared by partially wetting the inert support with a liquid such as water. This partially wet support should contain some liquid, but there should be no surface liquid visible. The partially wet support is contacted with a powder of the active ingredient composition, and the inert support is rolled in the active ingredients. The contact between the powder and inert support is easily accomplished by placing the support in a closed container, rotating the container in an inclined plane and adding portions of the powder. Preferably, substantially all of one portion of the powder is coated on the support before another portion is added.

More specifically, the catalyst of the invention is prepared by (1) contacting an essentially inert support of at least about 20 microns in diameter with an excess of liquid in such manner that the liquid is absorbed by the support to produce a wet support, (2) drying said wet support to produce a partially wet support, said partially wet support is defined as one that does not have the appearance of liquid on the outer surface of the support, but has at least some liquid absorbed on the support, (3) contacting the partially wet support with a powder consisting essentially of a catalytically active material and (4) gently agitating the mixture of partially-wet support and catalytically active oxide material to produce an inert support having a strongly adherent coating of the catalytically active oxide material on the outer surface of said support.

Alternately, the catalyst may be prepared by contacting an essentially inert support of at least 20 microns in diameter with a measured amount of liquid to produce a partially wet support, said support being one that does not have the appearance of liquid on the outer surface of the support, but has at least some liquid absorbed on the support, (2) contacting said partially wet support with a powder of the catalytically active oxide material and (3) gently agitating the mixture of partially wet support and catalytically active oxide material to produce an inert support having a strongly adherent coating of said material on the outer surface of said support.

After the above steps have been taken in the catalyst preparation, other drying and activation steps can be used to produce the desired catalyst.

The present invention employs a catalyst that combines the catalytically active material and inert support material in a manner that provides an especially effective catalyst for the oxidation of methacrolein to methacrylic acid.

The catalysts prepared by this process consist of the inert support and a strongly-adhering coat of the active catalytic ingredients on the outer surface of the support. The catalytic ingredients are maintained on the surface of the support, and there is essentially no impregnation of the active ingredients into the inert support. Thus, the catalysts of the invention are sharply contrasted with those catalyst techniques that impregnate an inert support with an active catalyst by contacting the support with a liquid or slurry of active ingredients.

The calcination of the catalyst usually is accomplished by heating the dry catalytic components at a temperature of about 200° C to about 700° C. The preferred procedure of the invention is wherein the catalyst is calcined at a temperature of 325° C to 425° C.

Specific catalysts of special interests are those wherein $b$ is 0.01 to 5, $c$ is 0.01 to 5, or $d$ is 0.001 to 5.

Especially preferred are catalysts wherein $b$ is 0.5 to 1.5, $c$ is 0.1 to 1.0 and $d$ is 0.1 to 1.0.

The process for the oxidation of acrolein to acrylic acid or the oxidation of methacrolein to methacrylic acid is well known in the art. Broadly, these reactions are carried out at a reaction temperature of 200° C to about 500° C. By the procedure of the invention, temperatures of 250° C to 370° C are preferred. These reactions can be conducted at atmospheric, superatmospheric or subatmospheric pressure using contact times of less than a second to a few seconds or more. The reaction is most suitably conducted in a fixed-bed reactor, although the reaction can also be conducted in a fluid-bed reactor provided that the support material is small enough in terms of particle size.

The three basic advantages of the present invention are (1) that the exotherm of the reaction is substantially lower, in other words the difference between the bath temperature and the reaction temperature is very much smaller than it is with the use of the pure catalytic material alone or even the catalytic material mixed with a support material; (2) it has been found that the per pass conversion obtained using the coated catalyst is as good or better than the uncoated catalysts; (3) it has been found that the coated catalysts in some cases essentially eliminate the formation of the undesirable byproduct acetic acid. With these advantages, the catalyst of the invention used in the production of unsaturated acids provides a very substantial advance in this commercial technology.

SPECIFIC EMBODIMENTS

Comparative Examples A to D and Examples 1 to 11: Preparation of Methacrylic Acid Using Coated Catalysts of the Invention Compared with Use of Uncoated Catalysts Comparative Examples A to D and Example 1

The active catalytic material of the formula $Mo_{12}P_{1.32}As_{0.5}Cu_{0.25}O_f$ was prepared as follows:

A solution consisting of 105.9 g. of ammonium heptamolybdate, $(NH_4)_6Mo_7O_{24}.4H_2O$, and 600 mls. of distilled water was boiled with stirring. To this solution was added 3.97 g. of ammonium arsenate, $NH_4H_2AsO_4$ and heating was resumed for 20 minutes; the color was white. Upon the addition of 2.5 g. of copper acetate, the color changed to light blue. To this mixture was added 7.6 g. of phosphoric acid, $H_3PO_4$ (85% solution), and 10 minutes later 2.5 g. of hydrazine hydrate was added to give a dark blue solution which was evaporated to a thick paste, dried overnight at 120° C.

COMPARATIVE EXAMPLE A $Mo_{12}P_{1.32}As_{0.5}Cu_{0.25}O_f$

This catalyst was prepared from a portion of the active catalytic material prepared above. The catalyst was ground and screened to 14/30 mesh size.

COMPARATIVE EXAMPLE B

25% $Mo_{12}P_{1.32}As_{0.5}Cu_{0.25}O_f$ + 75%$Al_2O_3$ (impregnated)

This catalyst was prepared by impregnating a portion of the catalyst solution on Norton SA-5209 ⅛ inch Alundum balls (low surface area alumina) before drying.

COMPARATIVE EXAMPLE C

25% $Mo_{12}P_{1.32}As_{0.5}Cu_{0.25}O_f$ + 75% $Al_2O_3$ (co-gelled)

This catalyst was prepared by mixing a colloidal alumina material, Q-Loid A-30, with a portion of the catalyst solution, drying the resulting product, and screening to 14/30 mesh.

COMPARATIVE EXAMPLE D

25% $Mo_{12}P_{1.32}As_{0.5}Cu_{0.25}O_f$ + 75% $Al_2O_3$ (co-mixed)

This catalyst was prepared by mixing a fine mesh $Al_2O_3$, Norton BA-106, with a portion of the catalyst solution and drying the resulting product.

EXAMPLE 1

25% $Mo_{12}P_{1.32}As_{0.5}Cu_{0.25}O_f$ + 75% $Al_2O_3$ (coated)

This catalyst was prepared by coating the active catalytic material on 10/30 mesh Norton SA 5223 ⅛ inch Alundum balls by taking 50 g. of Alundum, wetting the Alundum with 1.8 cc. of water and adding 16.7 g. of active catalyst in five equal portions. During and after each addition, the Alundum was rolled in a glass jar. Hard uniform coated catalysts were obtained that consisted of the Alundum support with a continuous, strongly adhering cost of the active catalyst.

EXAMPLE 2

25% $Mo_{12}P_{1.0}As_{0.5}Cu_{0.25}O_f$ + 75% Alundum (coated)

This catalyst was prepared in the same manner described above, except 5.8 g. of phosphoric acid were employed. The catalyst was coated on Alundum in the same manner described in Example 1.

Comparative Examples E to T and Examples 3 to 6 Effect of Coating on Performance of Catalyst of $Mo_{12}P_{1.32}As_{0.5}Cu_{0.25}O_f$ in the Preparation of Methacrylic Acid The catalysts were prepared in the same manner as shown above using the appropriate ratios of ingredients. Each catalyst was calcined 1 hour at 370° C in 40 ml./min. air.

A portion of these catalyst particles was charged to a 20 cc. fixed-bed reactor consisting of a 1.3 cm. stainless steel tubing equipped with a 0.3 cm. axial thermowell. However, a 0.15 cm. thermocouple was employed in Examples K to N. The reactor was heated to reaction temperature under a flow of air and then a feed of methacrolein/air/nitrogen/steam of 1/5.7/4.6/8.7 was fed over the catalyst at an apparent contact time of 2 to 3 seconds. The reactor was run under the reaction conditions and performance was evaluated by collecting and analyzing the products. The reaction conditions and results of the experiments are shown in TABLE I. The following definitions are used in measuring the carbon atoms in the feed and the products.

$$\% \text{ single pass yield} = \frac{\text{Moles of Methacrylic Acid Recovered}}{\text{Moles of Methacrolein in the Feed}} \times 100$$

$$\text{Total Conversion} = \frac{\text{Moles of Methacrolein Reacted}}{\text{Moles of Methacrolein in the Feed}} \times 100$$

$$\text{Selectivity} = \frac{\text{Single Pass Yield}}{\text{Total Conversion}} \times 100$$

TABLE I

Effect of Coating on Performance of the Catalyst
$Mo_{12}P_{1.0}As_{0.5}Cu_{0.25}O_f$ in the Preparation of Methacrylic Acid

| Example | Catalyst | Temperature, °C Bath | Exotherm | Methacrylic Acid | Acetic Acid | Conversion | Selectivity |
|---|---|---|---|---|---|---|---|
| Comp E | 100% Active | 298 | 299 | 24.1 | 1.1 | 31.5 | 76.0 |
| F | " | 323 | 330 | 47.0 | 2.9 | 63.0 | 75.0 |
| G | " | 332 | 335 | 59.0 | 3.4 | 76.0 | 78.0 |
| H | " | 338 | 346 | 57.0 | 4.3 | 79.0 | 72.0 |
| I | " | 343 | 356 | 60.0 | 5.4 | 86.0 | 71.0 |
| Comp J | 25% Active (Impregnated) | 323 | 323 | 51.0 | 1.3 | 56.0 | 91.0 |
| K | " | 343 | 343 | 49.2 | 1.7 | 58.6 | 85.0 |
| L | " | 349 | 350 | 63.0 | 4.9 | 76.6 | 82.0 |
| M | " | 360 | 361 | 69.8 | 4.5 | 86.6 | 81.0 |
| N | " | 377 | 379 | 64.7 | 6.9 | 91.5 | 41.0 |
| Comp O | 25% Active (co-gelled) | 268 | 274 | 7.8 | 0.8 | 17.0 | 46.0 |
| P | " | 291 | 299 | 12.9 | 2.5 | 35.0 | 37.0 |
| Q | " | 343 | 364 | 13.1 | 2.3 | 46.0 | 28.0 |
| Comp R | 25% Active (co-mixed) | 338 | | 21.8 | 1.8 | 35.7 | 61.0 |
| S | " | 349 | 356 | 35.0 | 2.4 | 51.0 | 68.0 |
| T | " | 363 | 370 | 30.7 | 3.5 | 69.4 | 44.0 |
| 3 | 25% Active (coated) | 313 | 315 | 75.5 | 2.3 | 83.0 | 90.6 |
| 4 | " | 316 | 318 | 65.4 | 1.3 | 78.5 | 84.6 |
| 5 | " | 332 | 334 | 73.3 | 4.1 | 89.0 | 82.0 |
| 6 | " | 344 | 348 | 72.4 | 6.6 | 97.0 | 73.8 |

EXAMPLES 7 TO 11

The catalyst of the formula 25% $Mo_{12}P_{1.0}As_{0.5}Cu_{0.25}O_f$ + 75% Alundum prepared in accordance with Example 2 was reacted with methacrolein in the same manner described above. The reaction conditions and the results of the experiments are shown in TABLE II.

TABLE II

Performance of the Catalyst
25% $Mo_{12}P_1As_{0.5}Cu_{0.25}O_f$ + 75% Alundum (Coated)
In the Preparation of Methacrylic Acid

| Example | Reaction Temp. °C | Results, % Total Conversion | Methacrylic Acid | Selectivity |
|---|---|---|---|---|
| 7* | 329 | 72.2 | 60.5 | 83.8 |
| 8 | 336 | 85.0 | 70.0 | 82.0 |
| 9 | 349 | 93.0 | 75.0 | 80.6 |
| 10 | 363 | 93.7 | 70.0 | 74.6 |
| 11 | 354 | 93.8 | 76.6 | 81.5 |

*Catalyst was not completely activated.

We claim:

1. In the process for the preparation of acrylic acid or methacrylic acid by the oxidation of acrolein or methacrolein in the vapor phase with molecular oxygen in the presence of an oxide or oxide complex active catalyst of the formula $$Mo_{12}P_bAs_cCu_dO_f$$

wherein
  b, c and d are numbers from 0.001 to 10;
  f is the number of oxygens required by the valence states of the other elements present,
at an elevated temperature of about 200° to about 500° C., the improvement comprising:
  using a coated catalyst consisting essentially of an inert support material having a diameter of at least 20 microns and an outer surface and a continuous coating of said active catalyst on said inert support strongly adhering to the outer surface of said support wherein said coated catalyst is prepared by partially wetting the support with water and rolling the partially wet support in a powder of the active catalyst.

2. The process of claim 1 wherein the active catalyst is about 10 to about 100 percent by weight of the inert support.

3. The process of claim 1 wherein the inert support is selected from the group consisting of silica, Alundum, alumina, alumina-silica, silicon carbide, titania and zirconia.

4. The process of claim 1 wherein the catalyst is calcined at a temperature of 325° C to 425° C.

5. The process of claim 1 wherein the reaction temperature is 250°–370° C.

6. The process of claim 1 wherein b is 0.01 to 5.

7. The process of claim 1 wherein c is 0.01 to 5.

8. The process of claim 1 wherein d is 0.001 to 5.

9. The process of claim 1 wherein b is 0.5 to 1.5, c is 0.1 to 1.0 and d is 0.1 to 1.0.

10. The process of claim 1 wherein the inert support has a particle size of about 0.2 cm. to about 2 cm.

11. The process of claim 1 wherein the catalyst employed is 25%$Mo_{12}P_{1.0}As_{0.5}Cu_{0.25}O_f$ + 75% Alundum.

12. The process of claim 1 wherein the oxidation is carried out in the presence of steam.

13. The process of claim 1 wherein methacrolein is reacted.

* * * * *